US009128063B2

United States Patent
Dooley

(10) Patent No.: US 9,128,063 B2
(45) Date of Patent: Sep. 8, 2015

(54) NON-CONTACT STRESS MEASURING DEVICE

(75) Inventor: Kevin Allan Dooley, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 537 days.

(21) Appl. No.: 12/953,557

(22) Filed: Nov. 24, 2010

(65) Prior Publication Data

US 2012/0126833 A1 May 24, 2012

(51) Int. Cl.
*G01R 27/28* (2006.01)
*G01N 27/90* (2006.01)
*G01R 27/26* (2006.01)
*G01N 3/06* (2006.01)
*G01L 1/12* (2006.01)
*G01L 3/10* (2006.01)

(52) U.S. Cl.
CPC .............. *G01N 27/90* (2013.01); *G01L 1/127* (2013.01); *G01L 3/105* (2013.01); *G01N 3/066* (2013.01); *G01R 27/2611* (2013.01); *G01N 2203/0075* (2013.01)

(58) Field of Classification Search
CPC .... G01R 27/2611; G01R 17/12; G01R 27/08; G01L 3/105; G01L 5/0047; G01N 27/9046; G01N 27/90; G01N 3/066; G01N 2203/0075
USPC .................................................. 324/654, 657
See application file for complete search history.

(56) References Cited

U.S. PATENT DOCUMENTS

| 4,107,605 | A | * | 8/1978 | Hudgell | ........................ 324/220 |
| 4,528,856 | A | | 7/1985 | Junker et al. | |
| 4,746,858 | A | | 5/1988 | Metala et al. | |
| 5,083,468 | A | * | 1/1992 | Dobler et al. | ............ 73/862.331 |
| 5,144,846 | A | * | 9/1992 | Klauber et al. | ........... 73/862.336 |
| 5,184,071 | A | | 2/1993 | Tasca | |
| 5,193,395 | A | | 3/1993 | Chern et al. | |
| 5,329,230 | A | | 7/1994 | Viertl et al. | |
| 5,431,063 | A | * | 7/1995 | Yasui | ........................ 73/862.333 |
| 5,610,515 | A | | 3/1997 | Soules | |
| 5,898,302 | A | * | 4/1999 | Soules | .......................... 324/209 |
| 7,159,470 | B2 | | 1/2007 | Saguto | |
| 7,362,096 | B2 | * | 4/2008 | Oberdier et al. | .............. 324/209 |
| 7,526,964 | B2 | | 5/2009 | Goldfine et al. | |

FOREIGN PATENT DOCUMENTS

JP      2001235375 A      8/2001

OTHER PUBLICATIONS

Abstract of: ASME Product Catalogue; 2001 Residual Stress Measurement and General Nondestructive Evaulation; D. E. Bray; Proceedings of the ASME Pressure Vessels and Piping Conference, Jul. 22-26, 2001, Atlanta, Georgia.

(Continued)

*Primary Examiner* — Amy He
(74) *Attorney, Agent, or Firm* — Norton Rose Fulbright Canada LLP

(57) ABSTRACT

Apparatuses and methods for measuring stress or strain in a conductive material without physical contact with the material are provided. The device comprises an inductor circuit configured to induce an alternating current into the material along a first path; and a detector configured to detect a signal representative of the stress in the material along the first path when current is induced in the material.

8 Claims, 12 Drawing Sheets

(56) References Cited

OTHER PUBLICATIONS

Advances in Eddy Current Measurement of Residual Stress; D. Barac, W. Katcher, and J. Soules; Cleveland State University, Advanced Manufacturing Center, 1752 East 23rd St., Cleveland, OH 44114 U.S.A.; The 7th International Conference on Shot Peening; ICSP(7); Institute of Precision Mechanics; Warsaw, Poland; Sep. 28-Oct. 1, 1999; pp. 326-334.

* cited by examiner

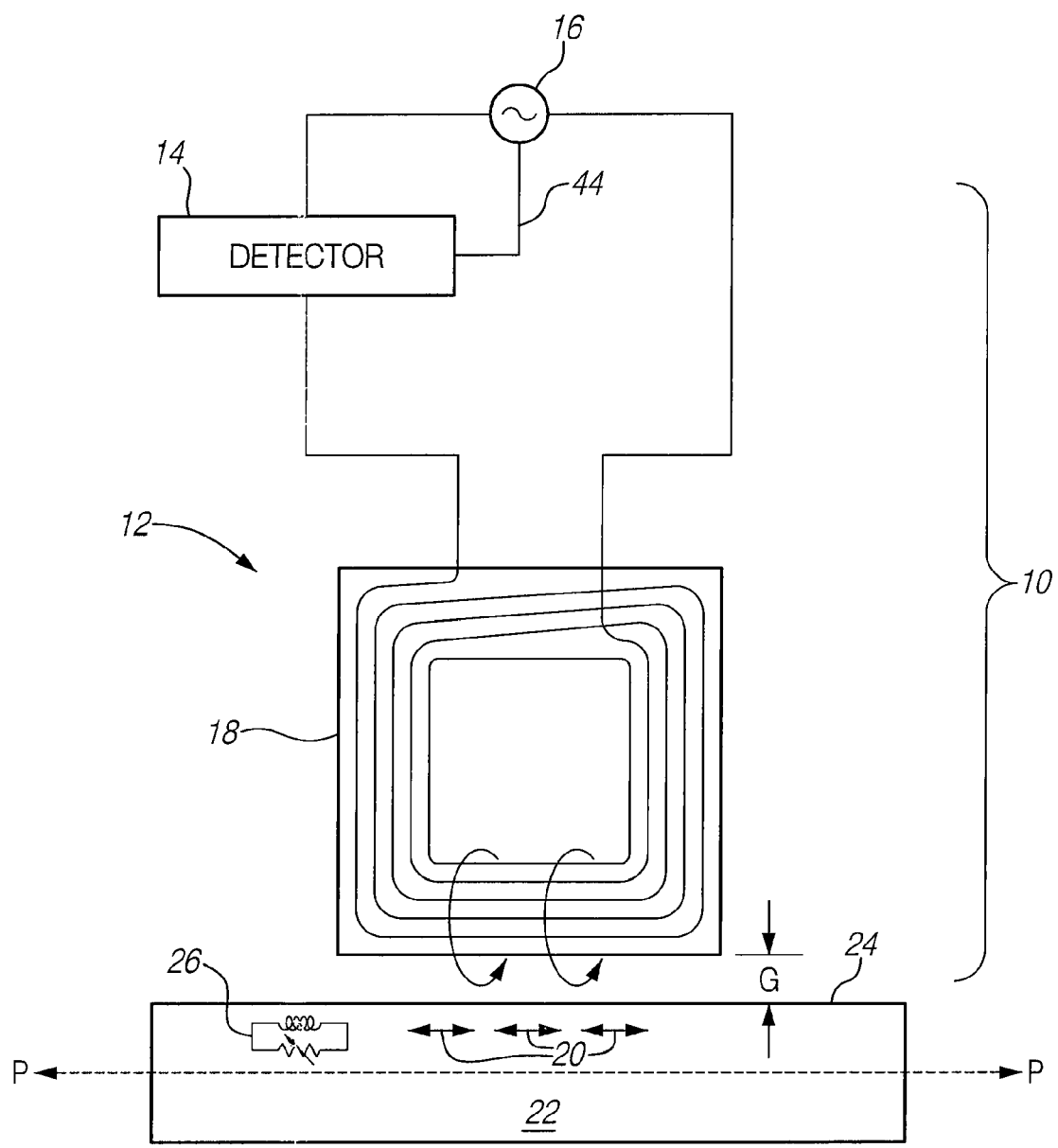

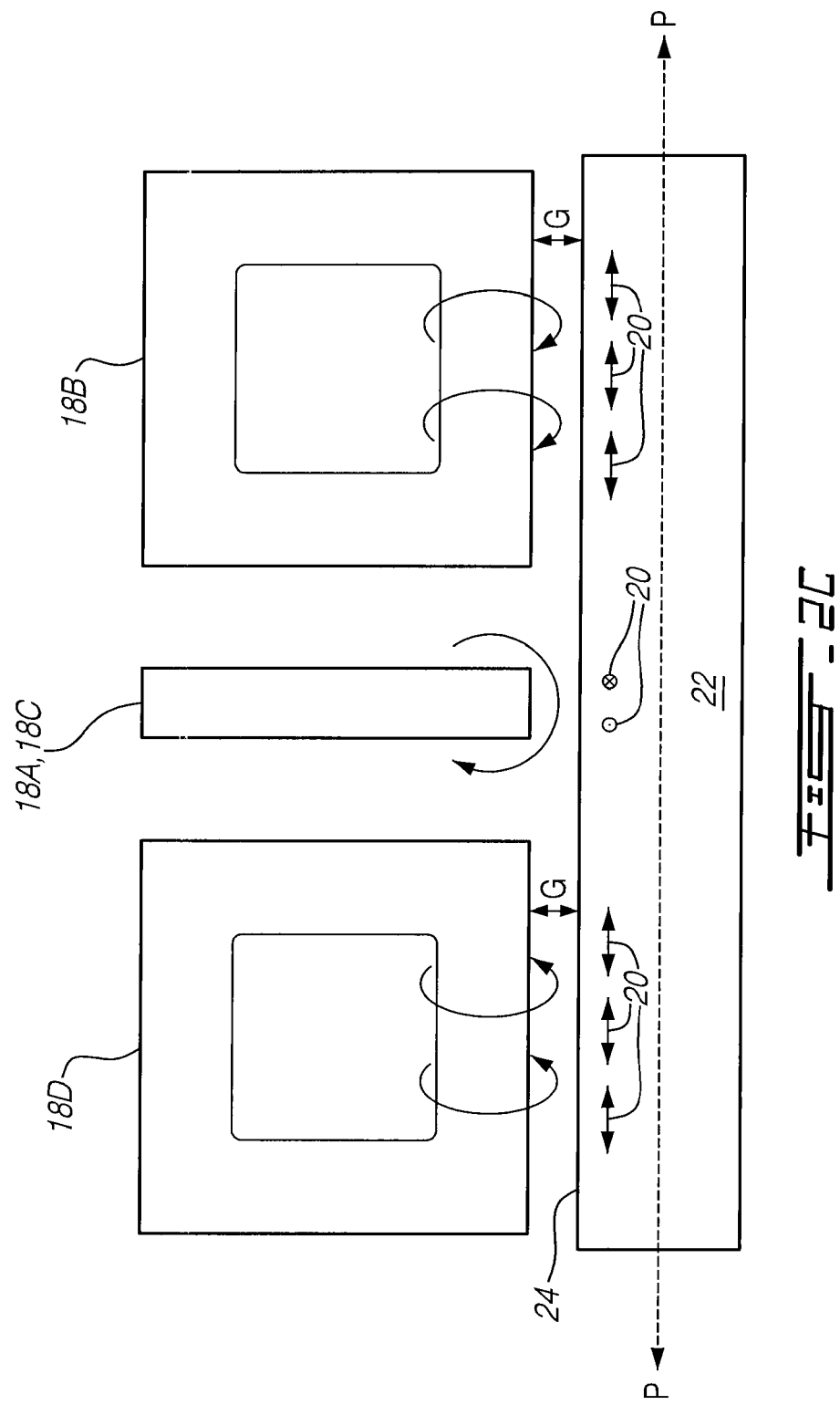

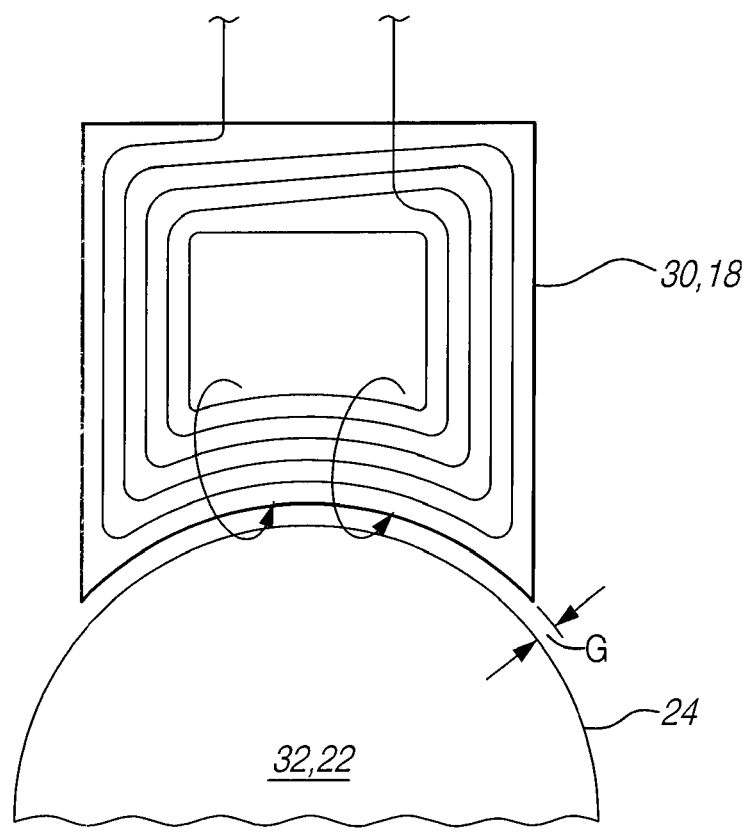

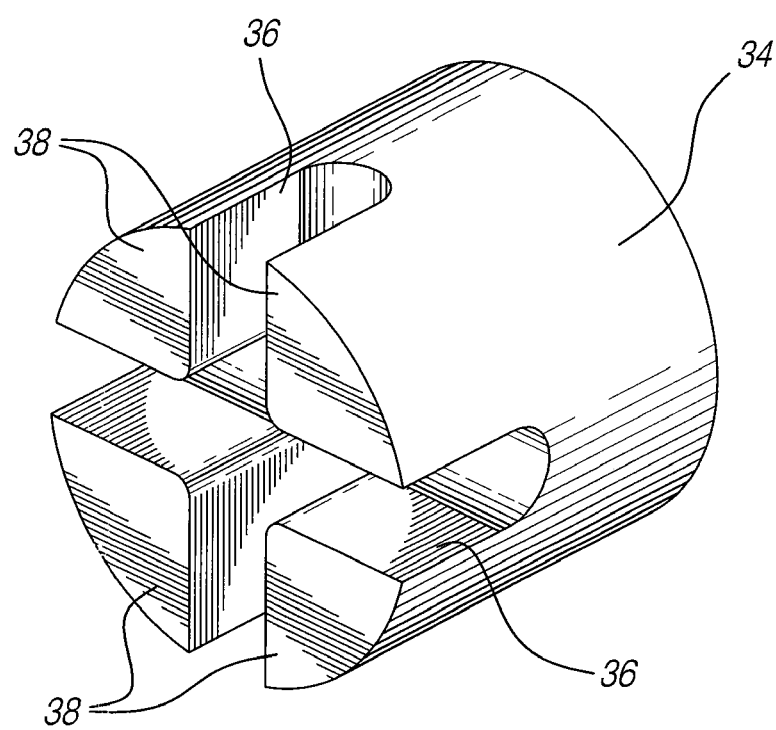
_FIG._5

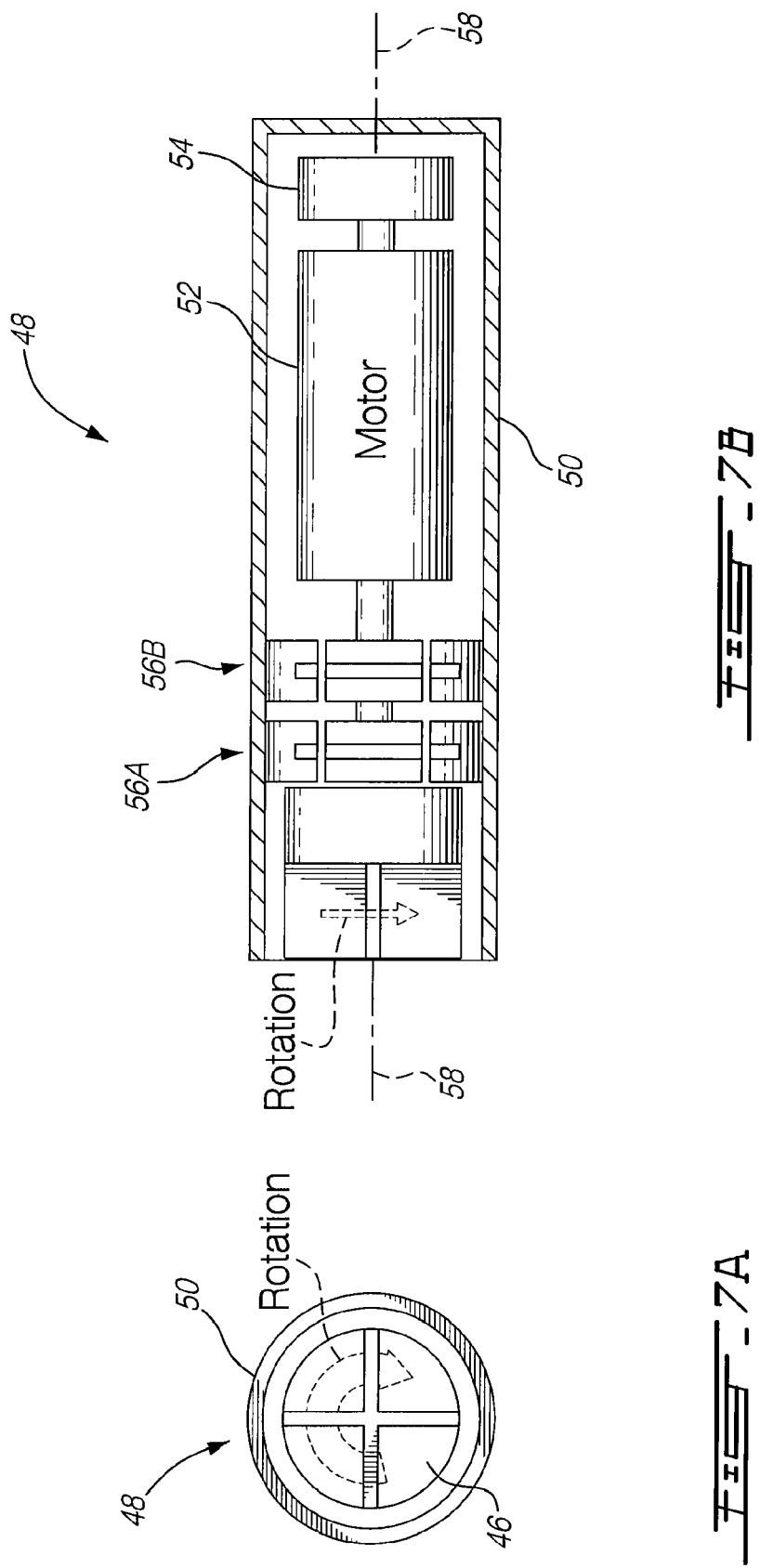

NON-CONTACT STRESS MEASURING DEVICE

TECHNICAL FIELD

The disclosure relates to methods and apparatus for measuring stress and strain in electrically conductive materials.

BACKGROUND OF THE ART

Non-destructive inspection of materials using eddy currents are known. Such methods may be used to detect flaws such as cracks in components. Some methods make use of flat spiral-shaped induction coils to detect the presence of residual stresses in a material. However, these methods do not allow for either the direction or magnitude of strain or stress in a component to be resolved.

Improvement in non-contact stress/strain measurement methods is therefore desirable, for these and other reasons.

SUMMARY

The disclosure describes apparatuses, systems, devices, and processes for measuring stress and strain in electrically conductive materials.

In various aspects, for example, the disclosure describes apparatuses, systems, devices, and processes for measuring stress in conductive material without physically contacting the material.

Thus, in one aspect, the disclosure describes an apparatus for measuring stress in conductive material without physically contacting the material. The apparatus may comprise: an inductor circuit configured to induce an alternating current along a first path in the material; and a detector connected to the inductor circuit and configured to detect a signal representative of the stress in the material along the first path when current is induced in the material.

In another aspect, the disclosure describes a non-contact stress measuring device that may comprise: first means for inducing an alternating current in a material along a first path; second means for inducing an alternating current in the material along a second path; and means for detecting a signal representative of the differential stress in the material along the first path and the second path.

In another aspect, the disclosure describes a method for obtaining a measurement representative of a stress in a material. The method may comprise: inducing an alternating current in the material along a first direction; and detecting a signal representative of the stress in the material along the first direction.

In a further aspect, the disclosure describes a stress measuring device for measuring stress in conductive material. The device may comprise: an inductor circuit having first, second, third and fourth inductors arranged in a Wheatstone bridge and configured to induce current in the material along a first path, second path, third path and fourth path respectively; and a detector connected to the inductor circuit and configured to detect a signal representative of an imbalance in the Wheatstone bridge.

Further details of these and other aspects of the subject matter of this application will be apparent from the detailed description and drawings included below.

DESCRIPTION OF THE DRAWINGS

Reference is now made to the accompanying drawings, in which:

FIG. 1 is a schematic elevation view of a stress measuring device according to one embodiment;

FIG. 2C is a schematic elevation view of the inductors of the device of FIG. 2A;

FIG. 3 is a schematic elevation view of an inductor used to measure stress in a component having a curved surface;

FIG. 5 is an isometric view of the flux guiding member of FIG. 4;

FIG. 6 is an elevation view of the probe of FIG. 4 positioned near a component;

FIG. 7A is schematic front elevation view of a probe positioning system comprising the probe of FIG. 4;

FIG. 7B is a schematic side elevation view of the probe positioning system of FIG. 7A;

DETAILED DESCRIPTION OF THE PREFERRED EMBODIMENTS

Figure 2A:
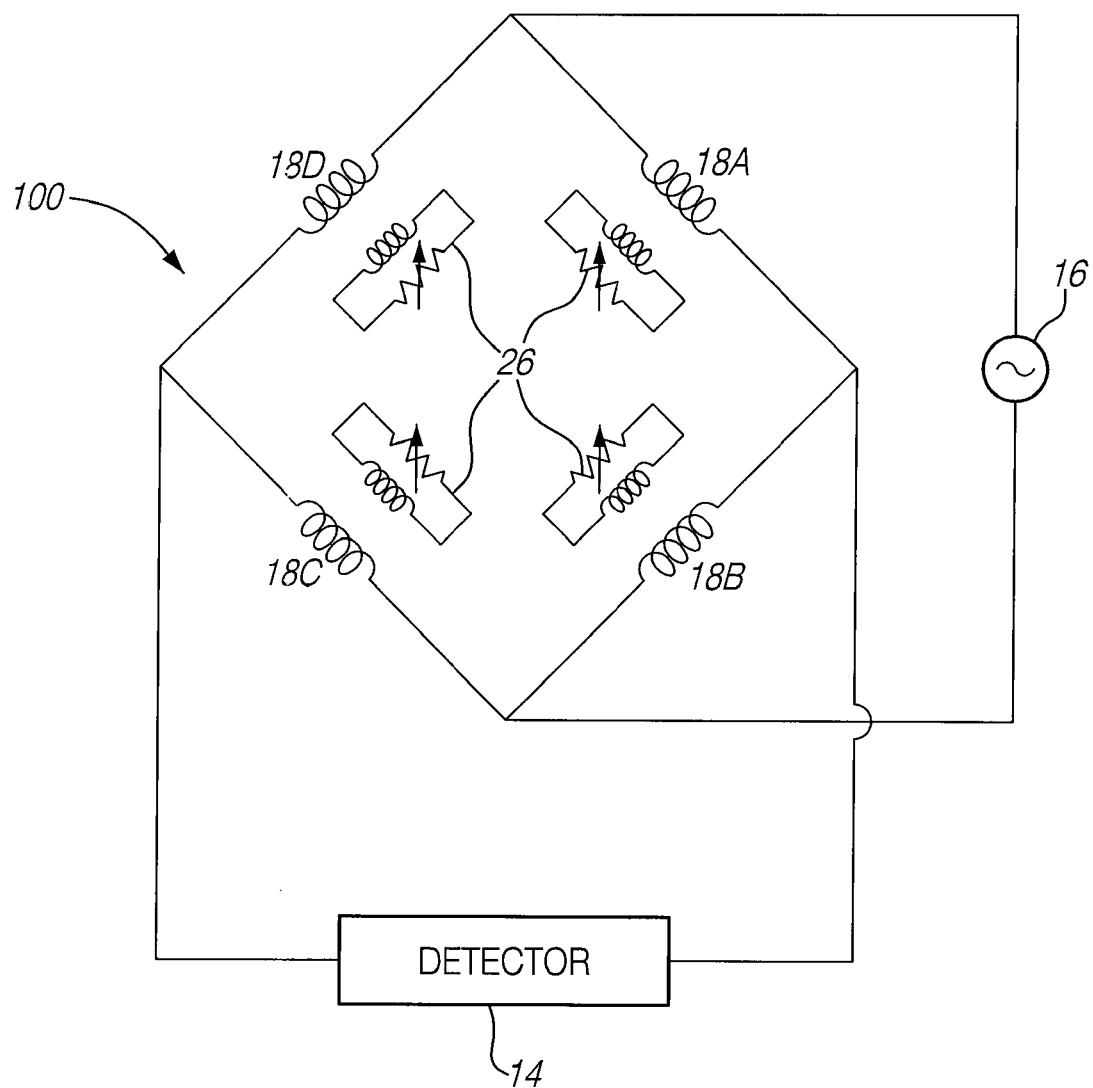
FIG. 2A is a schematic representation of a stress measuring device according to another embodiment.

Various aspects of preferred embodiments are described through reference to the drawings.

As will be understood by those skilled in the relevant arts, stresses and strains in deformable materials are in general inseparably associated with each other. In many cases they are related to each other according to known relationships, such as through Young's modulus. Thus the measurement of stresses and strains is often physically equivalent, or strongly related. For example, measurement of a strain in an object is equivalent, or strongly related, to determination of stresses. Discussion herein is cast generally in terms of stress, but should be interpreted and understood as applying to both stress and strain, as applicable, accordingly.

FIG. 1 shows a stress measuring device 10 that may be used for measuring stress (and/or strain) in a particular direction or along a particular path in an electrically conductive material such as a component 22 without physical contact with the material. Device 10 may comprise an inductor circuit 12 and a detector 14. Device 10 may be connected to alternating current (AC) source 16. Alternatively, AC source 16 may be incorporated into device 10 in the form of a battery together with suitable power conditioning equipment.

Inductor circuit 12 may comprise one or more inductors 18 configured to receive alternating current from AC source(s) 16 and induce current(s), represented by arrows 20, in the conductive component 22. Induced current(s) 20 may flow along path(s) that are substantially parallel to (e.g. mirror image of) the current flowing in inductor 18. For example, such a path may be substantially parallel to direction P.

Detector(s) 14 may comprise, for example, one or more current measuring sensors. Such current sensor(s) may have the ability to provide both the real part and the imaginary part of the current in relation to AC source(s) 16. Accordingly, detector 14 may also be connected to source 16 via link 44. For example, a commercially available detector such as model number US-454 manufactured by UNIWEST under the trade name EDDYVIEW may be used.

Figure 2B:
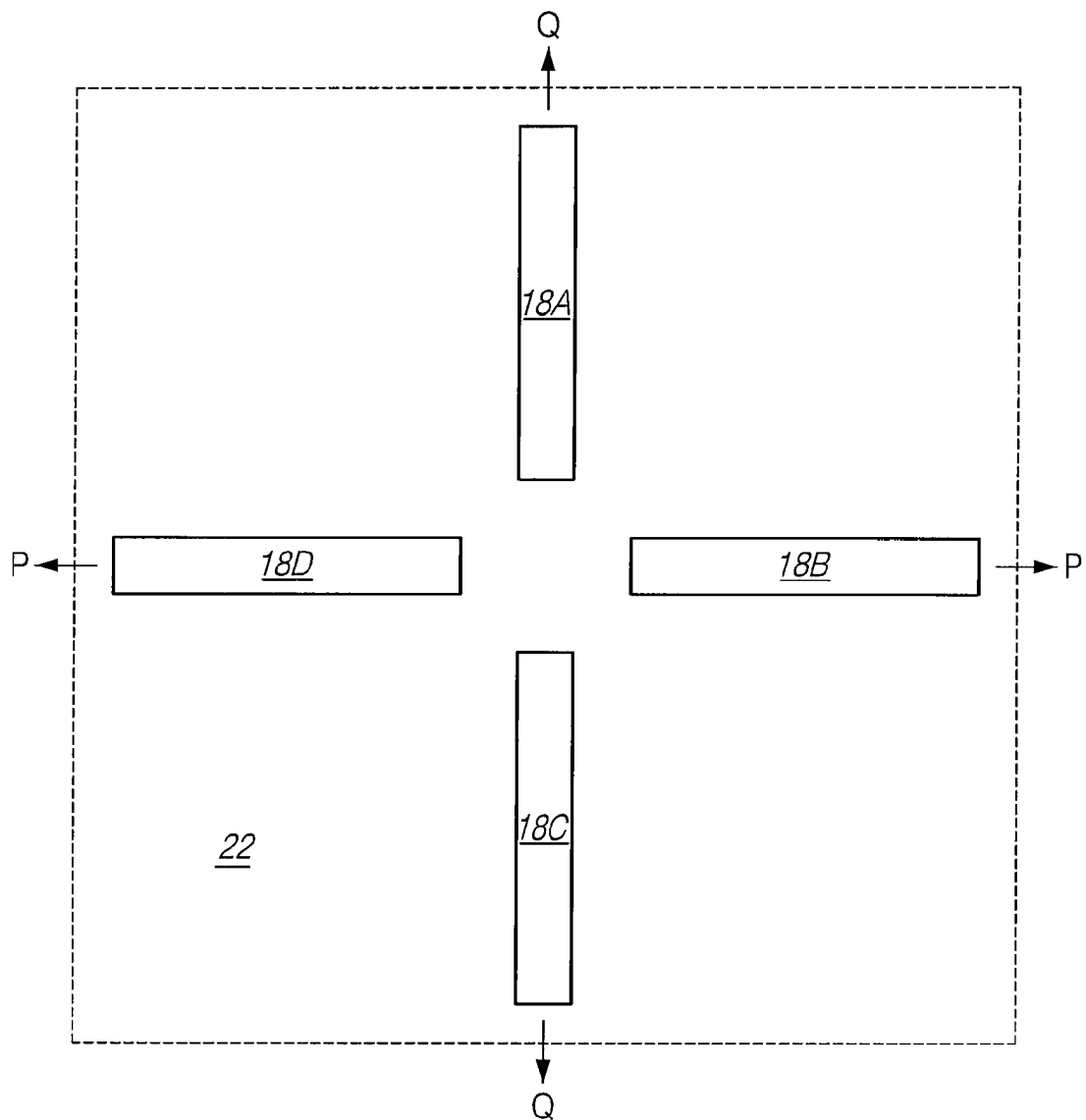
FIG. 2B is a schematic plan view of inductors of the device of FIG. 2A.

FIG. 2A-2C show a stress measuring device 100, according to another embodiment. In the embodiment shown, device 100 comprises a plurality of inductors 18A-18D arranged in a Wheatstone bridge configuration, as shown schematically in FIG. 2A. In the embodiment shown, four inductors 18A-18D are provided. Detector 14 used in conjunction with inductors 18A-18D arranged in a Wheatstone bridge configuration may comprise a voltage measuring device. Device 10, 100 may also comprise a display (not shown) for presenting measurements representative of stress/strain in component 22 to an operator of device 10, 100.

FIGS. 2B and 2C show an example configuration of four inductors 18 in relation to each other. Inductors 18 may be oriented in any suitable manner to induce current along differing paths or directions, so that the paths or directions of stresses or strains can be resolved, as for example using algebraic or other means. For example, inductors 18A-18D may be oriented so that inductors 18A and 18C induce current in component 22 along respective paths substantially parallel to direction Q and that inductors 18B and 18D induce current in component 22 along respective paths substantially parallel to direction P. For illustrative purposes, component 22 may in this way be considered analogous to secondary circuit(s) 26 having resistance(s) that is/are reflected into induction circuit 12 via magnetic coupling to inductor(s).

The reflected resistance(s) of secondary circuit(s) 26 on respective inductors 18A-18D may be sensitive to distance G and the configuration of inductors 18A-18D. Accordingly inductors 18A-18D may have substantially identical configurations (i.e. coil shape and size, number of turns, wire size) except for their respective orientations and all be positioned at a substantially similar distance G from component 22. In an exemplary applications, inductors 18A-18D may each comprise 50 turns of #47 AWG enamel insulated wire. It may also be possible to have inductors 18A-18D positioned at different respective distances G but each of inductors 18A-18D would then have to be designed/configured to produce the same effective reflected resistance as the other of inductors 18A-18D.

Inductors 18A-18D may be configured and/or oriented in any suitable fashion to accommodate various shapes or configurations of components 22, and/or determination of the direction(s) of any stress(es) of interest. The number of inductors 18 provided may be varied. Partial or full Wheatstone bridge configurations, or other configurations, may be used, depending on the needs of specific applications. For example, some of inductors 18 may oriented to induce current along parallel, perpendicular, and/or otherwise angled paths. Some of inductors 18A-18D may, for example, be oriented along parallel paths but be spaced apart to measure differential stress along a common direction but at two different locations on component 22. A Wheatstone bridge arrangement of inductors 18A-18D and the substantially identical configuration of inductors 18A-18D may allow, for example, offset errors and/or temperature-related differences between inductors 18A-18D to be reduced or essentially eliminated. Inductors 18A-18D may be disposed relatively close together so that a relatively small volume of material may required for measurement and also that, depending on the specific application, the effects of temperature and/or other environmental or material variations on the measurements may be reduced.

FIG. 3 shows an example of an inductor 18, 30 according to further embodiments which may be used within devices 10, 100 to measure stress in a component 32 having a curved surface 24. Shape(s) for inductor(s) 18, 30 may be determined based on the shape of the component 22, 32 in which stress is to be measured. For example, component 22, 32 may be a rotating shaft, in which the stress (and strain) may be continuously monitored. Inductor(s) 18, 30 may be oriented and of suitable shape(s) to detect axial or torsional stress in component 32. For measuring torsional stress (torque) in a shaft, inductor 30 may be configured and oriented to induce a current along a path that is about 45 degrees from the axis of the shaft and along the periphery of the shaft.

Figure 4:
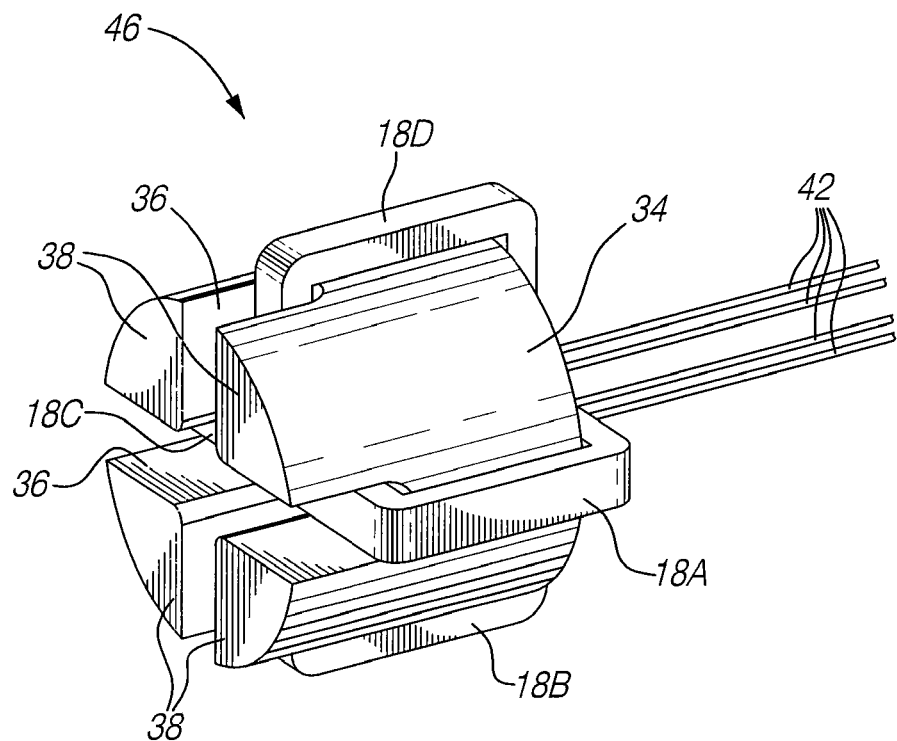
FIG. 4 is an isometric view of a probe comprising inductors such as those shown in FIG. 2A and a flux guiding member.
Figure 8:
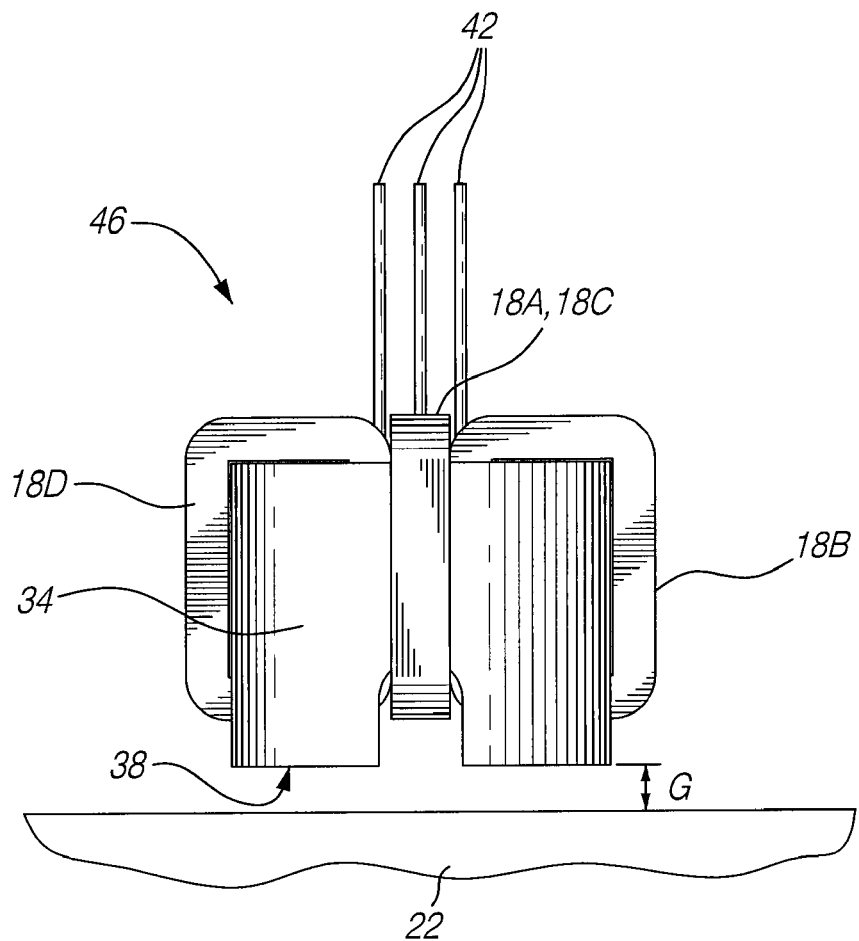
FIG. 8A is an exemplary graphical representation of an output of the probe positioning system of FIG. 7A relative to an orientation of the probe.
FIG. 8B is an exemplary polar plot representation of the output of the probe positioning system of FIG. 7A relative to an orientation of the probe.

FIGS. 4-6 show examples of inductors 18A-18D of a device 100 and a flux guiding member 34 configured in the form of probe a 46. Flux guiding member 34 may be electromagnetically coupled to inductors 18A-18D. Flux guiding member 34 is shown in isolation in FIG. 5 and may comprise, for example, a commercially-available ferrite bead modified to have slots 36 formed therein for receiving inductors 18A-18D. A commercially available ferrite bead such as for example, part number FB73-226-RC sold under the trade name DIGI-KEY may be modified and be suitable in some applications. Slots 36 may be formed in flux guiding member 34 using a conventional or other material removal process such as, for example, machining, cutting, grinding or electrical discharge machining (EDM).

Flux guiding member 34 may serve function(s) of concentrating and homogenizing a magnetic field (flux density) induced by conductors 18A-18D and directing magnetic flux towards an active volume of the target conductive component 22. Magnetic flux can have a tendency to enter or exit a component at an orientation normal to a surface through which the magnetic flux enters or exits. Accordingly, flux guiding member 34 can provide a guiding path for the magnetic flux and causes the magnetic flux to exit from and enter flux guiding member 34 through bottom surfaces 38. Bottom surfaces 38 may serve as pole pieces known in the relevant arts and used to direct/capture the magnetic flux to/from an active volume of material in component 22. The use of flux guiding member 34 may allow devices 10, 100 to provide a more accurate representation of the stress/strain along a specific direction or path of interest.

Those skilled in the relevant arts will appreciate that the shape and configuration of flux guiding member 34 may differ from that shown in FIGS. 4-6 depending, for example, on the specific application. A suitable flux guiding member could also be used in conjunction with device 10 of FIG. 1 or inductor 30, 18 of FIG. 3. For example, bottom surfaces 38 (i.e. pole pieces) may not necessarily be planar and may be configured in accordance with a contour of a specific conductive component 22 of interest. Slots 36 may have width(s) and depth(s) to receive inductors 18A-18D and may be designed based on the desired physical size of a probe 46. For example, a larger probe 46 may result in current(s) being induced in a larger volume of material in component 22. Inductors 18A-18D may be interconnected into a Wheatstone bridge configuration in proximity to inductors 18A-18D so as to facilitate the integration of inductors 18A-18D into a portable unit (not shown) and permit lead wires 42 to be twisted together.

Figure 7C:
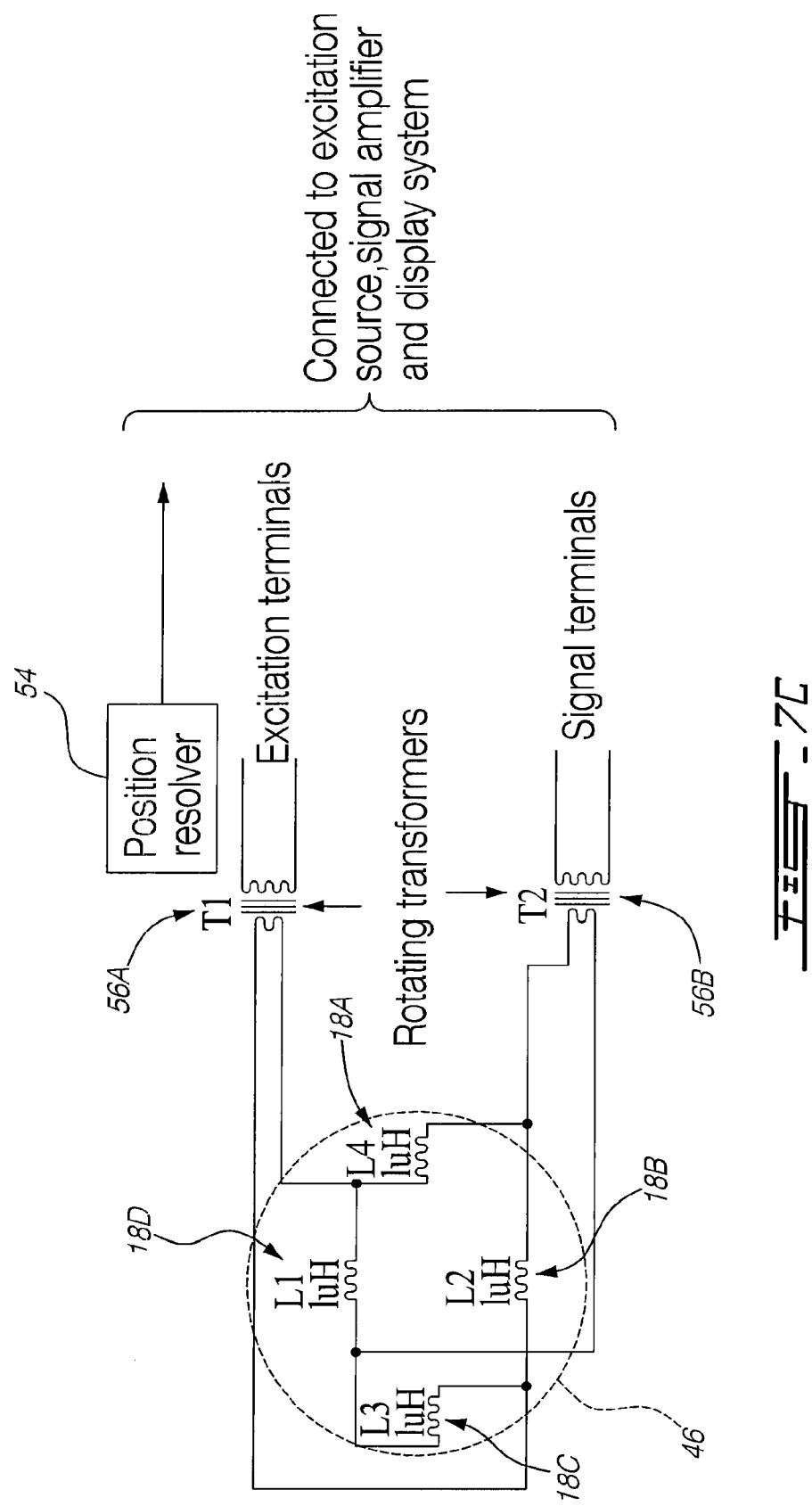
FIG. 7C is a schematic representation of the probe positioning system of FIG. 7A.

FIGS. 7A, 7B and 7C schematically show a probe positioning system, generally shown at 48, which may be part of or otherwise associated with devices 10, 100. Probe positioning system 48 may comprise housing 50 in which probe 46 (described above) may be housed along with motor(s) 52, position resolver(s) 54 and/or rotating transformer(s) 56A and 56B. Motor(s) 52 may be coupled to probe 46 so as to rotate probe 46 about its central axis 58. Position resolver(s) 54 may be coupled to motor(s) 52 so as to monitor the orientation of probe 46. Accordingly, probe 46 may be continuously rotated or may be rotated in a stepwise manner during stress/strain measurement in order to conveniently obtain stress/strain measurements along a desired orientation or path in component 22, 32. A control system (not shown) may be used to automatically control the orientation of probe 46 and cause stress/strain measurements to be taken at desired orientations and at desired intervals.

Rotating transformer(s) 56A may be used to transfer excitation signals to inductors 18A-18D from an AC source(s) not shown in FIGS. 7A-7C. Rotating transformer(s) 56B may be used to obtain output signal(s) from inductor(s) 18A-18D indicative of the stress/strain in component 22,32. As described herein, output from inductors 18A-18D may be detected using detector(s) 14 which may comprise a voltage measuring device. One or more signal amplifiers may be used in the detection of the output from inductors 18A-18D. Motor(s) 52 and mechanical connections between probe 46, motor 52 and position resolver 54 are not shown in FIG. 7C, as suitable arrangements for their incorporation will be immediately understood by those skilled in the relevant arts.

Figure 8A:
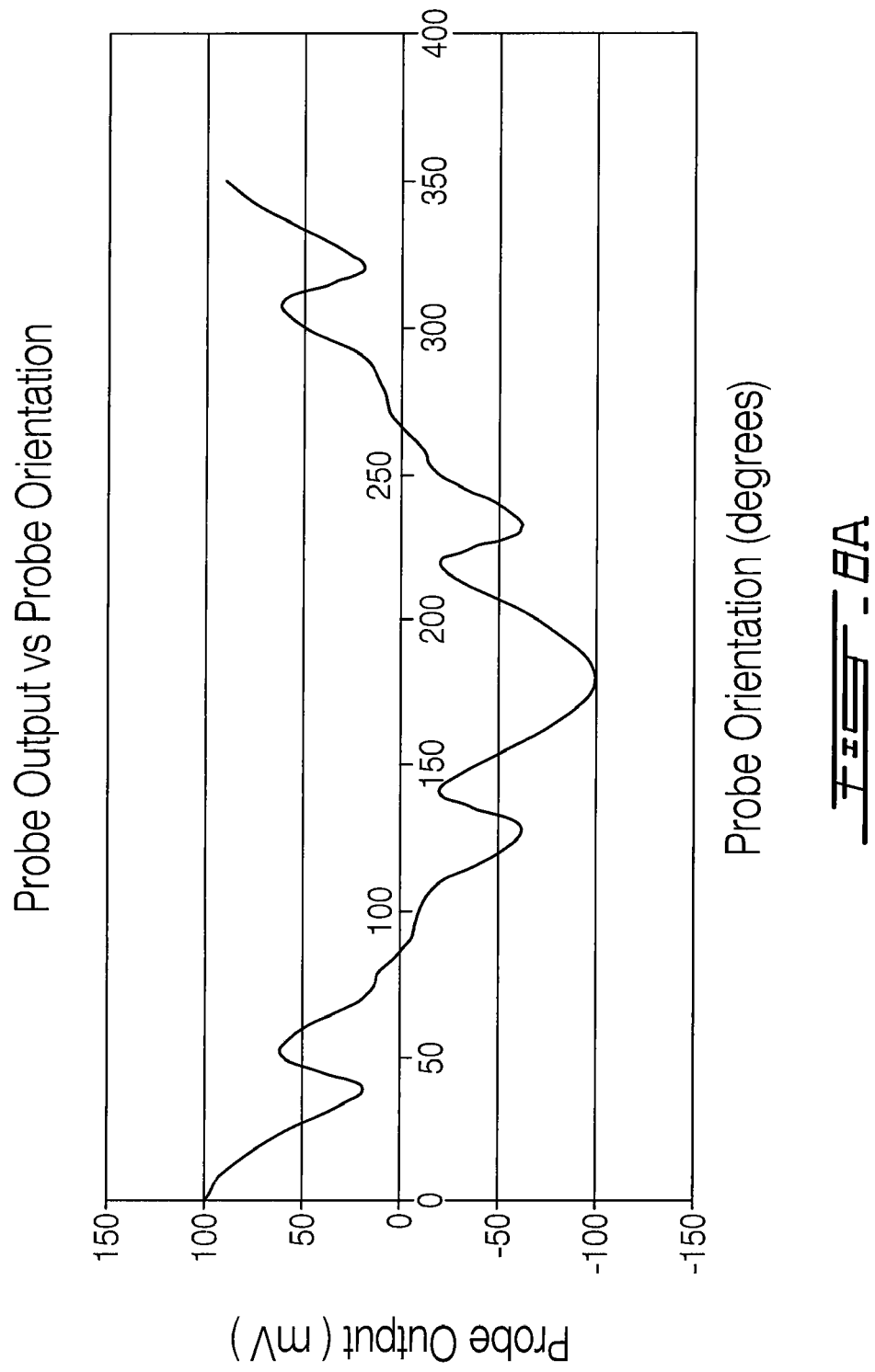
Figure 8B:
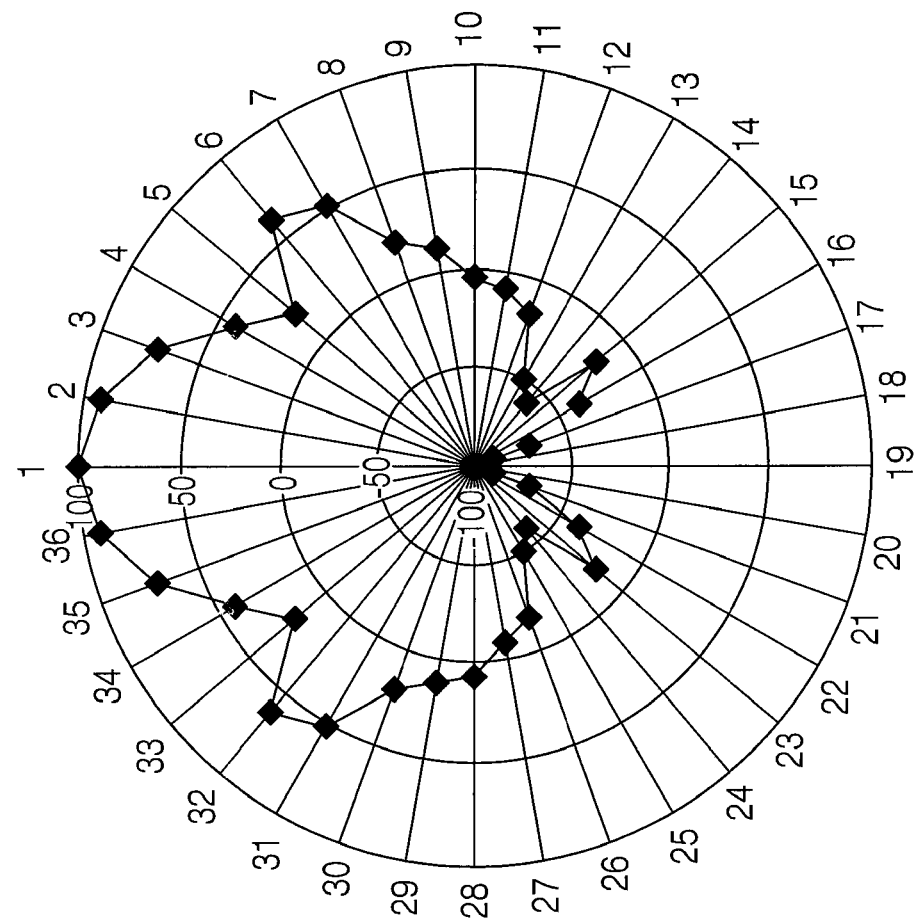

FIG. 8A shows an exemplary output (mV) from probe 46 as a function of probe orientation (degrees) in a X-Y graphical representation. FIG. 8B shows the same output (mV) from probe 46 as a function of probe orientation (degrees) in the form of a polar plot. The output from probe 46 in mV may be correlated to a representative stress (Pa or psi) value. The output from probe 46 may be presented on a display means such as a liquid crystal display (not shown) which may be part of or associated with probe positioning system 48.

In use, inductor(s) 18, or sets thereof, may be positioned at a distance G from one or more surfaces of a component 22, 32 to be substantially parallel to such surface(s). In cases where multiple identical inductors 18A-18D are used such as in device 100, all inductors 18A-18D may need to be positioned at a substantially same distance G from component 22. When using probe 46 of FIGS. 4 and 6, all four bottom surfaces 38 (pole pieces) may need to be positioned at a substantially same distance G. Accordingly, non-destructive stress measurements using devices 10, 100 may be conducted without physically contacting component 22. Alternatively and when flux guiding member 34 comprises a polymeric or other suitable coating, probe 46 may be place in physical contact with component 22, 32 (if appropriate) so that bottom surfaces 38 are electrically isolated from component 22, 32 by the polymeric coating.

When alternating current is driven into inductor(s) 18 using AC source 16, a magnetic field of continuously changing magnitude and direction can be generated in the vicinity of inductor(s) 18. The presence of conductive component 22 within the varying magnetic field can cause current(s) (i.e. eddy currents) 20 (FIG. 1) to be induced in component 22 in accordance with known electromagnetic principles. The shape(s) and/or orientation(s) of inductor(s) 18 may be adapted to induce current(s) 20 along one or more directions P in component 22. Depending on the configuration of component 22 and the direction(s) along which the stress is to be measured, current(s) 20 may be induced to flow along substantially linear and/or curved path(s). The flow of current(s) 20 in component 22 may be considered analogous to secondary circuit(s) 26 having resistance(s) that is reflected into induction circuit 12 via magnetic coupling to inductor(s) 18. Accordingly, the presence of component 22 and its electrical resistance may cause change(s) in the impedance of inductor(s) 18. The change in impedance of inductor(s) 18 may be detected using detector(s) 14.

The electrical resistance of a conductive material may vary with, and be correlated to, any strain present in the material, and therefore stress in the material. Accordingly, a change in impedance of an inductor 18 detected by a detector 14 can be representative of both the strain and the stress in the material of a component 22 along any path(s)/direction(s) in which current is induced. In an exemplary embodiment, a baseline impedance reading of an inductor 18 may be obtained using a baseline component (not shown) of known stress prior to taking a test impedance reading using component 22. The baseline component could, in such cases, conveniently be of the same or similar material as component 22. Differences between such baseline impedance reading and test impedance reading may be representative of the differential stress between the baseline component and component 22 along a path or direction in which current 20 is induced. Stress(es) detected in component 22 may be correlated to strain according to conventional or other suitable calculations. Alternatively, a baseline reading may be obtained using component 22 in an unloaded state while a test reading could be obtained using component 22 in a loaded state or vice versa. Hence, device 10 and inductor 18 could be used to detect a change in stress in component 22 in the event where component 22 is subject to loading/unloading.

A device 100 shown in FIGS. 2A-2C may make use of inductors 18A-18D for the purpose of detecting differential stress between two directions (e.g. P and Q) in a component 22, and for resolving the stress components that make up principal stresses in component 22. Inductors 18A-18D may be configured to have substantially the same impedance. Accordingly, a baseline impedance reading may not be required when a device 10, 100 is used, depending on the specific application. For example, device(s) 10, 100 may be used simply to detect a differential stress between directions P and Q in a component 22. Inductors 18A-18D may be arranged in a Wheatstone bridge configuration and detector(s) 14 may be configured to detect an imbalance in the impedance of the inductors 18A-18D. Such imbalance in the impedance of inductors 18A-18D may be indicative of a differential electrical resistance in the component 22 along directions P and Q. Hence, an imbalance in the impedance in the Wheatstone bridge may be indicative of a differential stress in a component 22 along any directions P and Q of interest.

For example, if a force along direction P is applied to a component 22, two of inductors 18A-18D may be used to provide a reference signal and the other two of inductors 18A-18D may be used to provide a signal representative of the change resistance of the material of component 22 due to the stress in the material of component 22 along direction P. Due to Poisson's effect, a force along direction P may also produce a stress in direction Q in accordance with Poisson's ratio. Accordingly, device(s) 10, 100 may be calibrated to take Poisson's effect into consideration based on the material that is tested. Device 100 may not be sensitive to stresses in component 22 if the stresses along directions P and Q are the same.

Inductors 18A-18D may be multi-turn coils having a coil axis that is substantially parallel to surface 24 of component 22 in which stress is to be measured. The frequency of the AC source 16 may be selected so that the current density is appropriately distributed within component 22. Selection of a suitable frequency may be done in accordance with known electromagnetic principles taking into consideration the skin effect. In particular, the frequency of AC source 16 may be selected according to the desired depth at which measurement is to be taken. The desired frequency of AC source 16 may differ for different applications and materials. For example, a frequency of about 50 Khz may be suitable in some applications. Depending upon the materials to be tested, and the configuration or geometry of such materials, some experimentation or analysis may be applied in determining an optimal frequency. Such experimentation or analysis will not trouble those skilled in the relevant arts, once they have been made familiar with this disclosure.

Using a probe positioning system 48 such as that shown in FIGS. 7A-7C, probe 46 may be continuously rotated during measurement or may be rotated in a stepwise manner (e.g. indexed) between consecutive measurements in order to conveniently obtain stress/strain measurements along a desired orientation or path in component 22, 32. A control system (not shown) may be used to drive electric motor 52 and automatically control the orientation of probe 46 and cause stress/strain measurements to be taken at desired orientations and intervals. Position resolver 54 may be used to control and monitor the orientation of probe 46. Accordingly, the output from probe 46 may obtained as a function of probe orientation as shown in FIGS. 8A and 8B. FIG. 8A shows an exemplary output (mV) from probe 46 as a function of probe orientation (degrees) in a X-Y graphical representation. Output (mV) from probe 46 in relation to probe orientation (degrees) may alternatively or in addition be presented in the form of a polar plot as shown in FIG. 8B.

The above description is meant to be exemplary only, and one skilled in the art will recognize that changes may be made to the embodiments described without departing from the scope of the invention disclosed. For example, the orientation and number of inductors used may differ depending of the application and the intent of the stress measurements. Also the shape of the inductors may be determined based on the shape of the component to be used for measurement. The inductors may also be integrated in a suitable stress measuring probe for portable use. Still other modifications which fall within the scope of the present invention will be apparent to those skilled in the art, in light of a review of this disclosure, and such modifications are intended to fall within the appended claims.

What is claimed is:

1. Apparatus for measuring stress in conductive material without physically contacting the material, the apparatus comprising:
    an inductor circuit comprising a first inductor, a second inductor, a third inductor and a fourth inductor arranged in a Wheatstone bridge configuration and configured to induce alternating current in the material along a first path, a second path, a third path and a fourth path respectively without physically contacting the material, the first path and the second path extending in different respective first and second directions; and
    a detector connected to the inductor circuit and configured to detect a signal representative of a differential stress in the material between the first direction and the second direction when current is induced in the material, the detector being configured to detect an unbalance in the Wheatstone bridge.

2. The apparatus as defined in claim 1, wherein the detector is configured to detect an impedance in the inductor circuit.

3. The apparatus as defined in claim 1, comprising a system for changing an orientation of the inductor circuit.

4. The apparatus as defined in claim 1, wherein the detector is configured to measure a differential impedance between the first inductor and the second inductor.

5. The apparatus as defined in claim 1, wherein the first path is substantially perpendicular to the second path.

6. The apparatus as defined in claim 1, further comprising a motor for changing an orientation of the inductor circuit relative to the material.

7. The apparatus as defined in claim 1, wherein the first path differs from the second path and the third path differs from the fourth path.

8. The apparatus as defined in claim 1, further comprising a flux guiding member coupled to inductor circuit.

* * * * *